(12) United States Patent
Chen et al.

(10) Patent No.: US 7,709,539 B2
(45) Date of Patent: May 4, 2010

(54) THERAPEUTIC USE OF RESVERATROL FOR HYPERGLYCEMIA

(75) Inventors: Jan-Kan Chen, Tao-Yuan (TW); Li-Man Hung, Tao-Yuan (TW)

(73) Assignee: Chang Gung University, Kwai-Shan, Tao-Yuan (TW)

( * ) Notice: Subject to any disclaimer, the term of this patent is extended or adjusted under 35 U.S.C. 154(b) by 852 days.

(21) Appl. No.: 10/916,317

(22) Filed: Aug. 11, 2004

(65) Prior Publication Data
US 2006/0034763 A1 Feb. 16, 2006

(51) Int. Cl.
*A61K 31/05* (2006.01)
*A61P 3/10* (2006.01)

(52) U.S. Cl. .................. 514/733; 514/866
(58) Field of Classification Search ........... 514/733, 514/866
See application file for complete search history.

(56) References Cited

U.S. PATENT DOCUMENTS

| | | | | |
|---|---|---|---|---|
| 5,264,221 | A | 11/1993 | Tagawa et al. | 424/450 |
| 5,283,330 | A | 2/1994 | Bhansali | 544/99 |
| 6,031,127 | A | 2/2000 | Yamamoto et al. | 562/443 |
| 6,063,820 | A | 5/2000 | Cavazza | 514/739 |
| 6,653,349 | B1 | 11/2003 | Cavazza | 514/547 |
| 6,716,883 | B1 | 4/2004 | Casper et al. | 514/733 |

OTHER PUBLICATIONS

Su et al., Am. J. Physiol. Endocrinol. Metab. (2006), vol. 290, E1339-E1346.*
Masiello, P. et al., "Experimental NIDDM. Development of a new model in adult rats administered streptozotocin and nicotinamide," Diabetes, vol. 47, pp. 224-229 (Feb. 1998).*
Rabinowitz, J.L. et al., "Changes in whole body lipid composition in a murine model of insulin-dependent diabetes mellitus," Metabolism, vol. 38(8), pp. 777-780 (Aug. 1989).*
Tsuji, A. et al., "Generation of nitric oxide from streptozotocin (STZ) . . . " Biochemical and Biophysical Research Communications, vol. 245, pp. 11-16 (1998).*
HCAPLUS abstract 1974:445768 (1974).*
HCAPLUS abstract 2000:4052 (2000).*
Medline abstract 2003607896 (2003).*
Medline abstract 2003586994 (2003).*
Medline abstract 1987189695 (1987).*
Medline abstract 1997414086 (1997).*
Medline abstract 1989245812 (1989).*

* cited by examiner

*Primary Examiner*—John Pak

(57) ABSTRACT

Resveratrol, an antioxidant found in various fruits, vegetables, grapes, and red wines, has been shown to have free radical scavenging, anti-inflammatory and anti-thrombogenic activities in biological systems. Moreover, resveratrol has also been shown to be a good cancer preventive chemical and has been recommended as a food supplement for health benefits. Resveratrol can effectively lower the blood sugar in both type 1 (insulin-dependent diabetes mellitus, IDDM) and type 2 (insulin-independent diabetes mellitus, NIDDM) diabetic rats. Resveratrol could also delay the onset of the insulin-resistant phenotype in experimental rats with prolonged injection of insulin. Further, resveratrol simultaneously slows down the body weight increment compared with untreated insulin resistant animals.

5 Claims, 6 Drawing Sheets

THERAPEUTIC USE OF RESVERATROL FOR HYPERGLYCEMIA

BACKGROUND OF THE INVENTION

1. Field of the Invention

The present invention relates to the therapeutic use of resveratrol in reducing blood sugar levels for both type 1 and type 2 diabetes mellitus (DM)

2. Description

Diabetes can be due to a deficiency of insulin or to a decreased responsiveness to insulin. Thus, diabetes is several diseases with different causes. Diabetes is classified into type 1 and type 2 based on how much insulin a person's pancreas is secreting. In type 1 diabetes mellitus (insulin-dependent diabetes mellitus, IDDM), insulin secretion is completely or nearly completely absent from the μ-cells of the islets of Langerhans, and Therapy with insulin is essential. In type 2 diabetes mellitus (insulin-independent diabetes mellitus, NIDDM), insulin is usually present at nearly normal or above normal levels. However, in about one third of NIDDM patients, insulin therapy is beneficial.

It was estimated that DM affects about 130 million people in developed countries worldwide, and by year 2025, about 300 million will be affected. Thus, the development of new effective antihyperglycemic drugs for both IDDM and NIDDM patients is of great medical importance. Currently, insulin injection is The only way to lower the plasma sugar for IDDM patients. For NIDDM patients, current treatment is the administration of sulfonylurea related drugs to stimulate insulin secretion by μ-cells or of biguanides to promote the response of peripheral tissue to insulin. Administration of insulin is beneficial to about one third of The NIDDM patients; however, the development of insulin-resistance may aggravate The problem. So far, no drug has been developed that could have therapeutic antihyperglycemic efficacy on both IDDM and NIDDM patients. Trans-resveratrol has antihyperglycemic effects on both IDDM and NIDDM rats. In addition, resveratrol also delays the onset of insulin-resistance in long term insulin administrated rats. Further, resveratrol also slows down the body weight increment compared with untreated insulin-resistant animals.

The medical community has a need for the development of resveratrol as an antihyperglycemic drug and as a healthy food supplement to lower the levels of plasma sugar in IDDM, NIDDM and obese people.

SUMMARY OF THE INVENTION

The main objective of the present invention is to provide the use of resveratrol as a antihyperglycemic drug for both type 1 and type 2 DM.

Resveratrol, an antioxidant found in various fruits, vegetables, grapes, and red wines, has been shown to have free radical scavenging, anti-inflammatory and anti-thrombogenic activities in biological systems. Moreover, resveratrol has also been shown to be a good cancer preventive chemical and has been recommended as a food supplement for health benefits. Resveratrol can effectively lower the levels of blood sugar in both type 1 and type 2 diabetic rats. Resveratrol also delays the onset of the insulin-resistant phenotype in experimental rats induced by prolonged injection of insulin. Further, resveratrol also slows down the body weight increment compared with untreated insulin-resistant animals.

METHODS

Animals and Treatment

Figure 1:
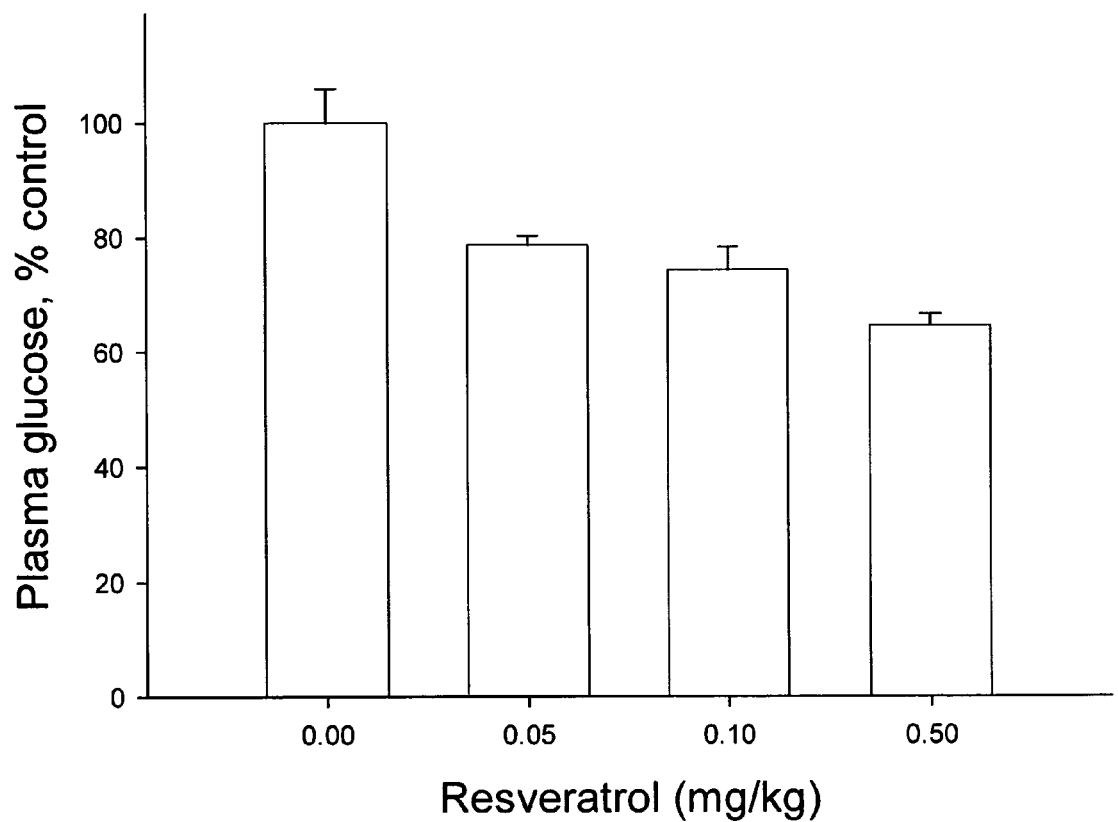
FIG. 1 is a bar graph of antihyperglycemic effect of resveratrol in normal SD rats.

Eight week-old Sprague Dawley (SD) rats (body weight from 200 gm to 250 gm) were maintained in the Animal Center of the Chang (Jung Memorial Hospital, under an ambient temperature of $25\pm1°$ C. and a light-dark period of 12 hrs. Animals were fed with normal chow and water.

Resveratrol was first dissolved in DMS0 and diluted to 0.05 mg, 0.1 mg and 0.5 mg per ml wit normal saline. Animals were fed with desired amounts of drug solutions though tubing from the mouth into the stomach.

Induction of Type 1 DM (IDDM)

Male rats were fasted for 72 hrs and anesthetized by intraperitoneal injection of pentobarbital at 30 mg/kg body weight. Animals were then injected with freshly prepared streptozotocin (STZ) solution at 65 mg/kg body weight intravenously. Three days later, blood sugar was measured. Animals with blood sugar levels above 400 mg/dl and symptoms of polyphagia, polyuria and polydipsia are classified as being induced to IDDM.

Induction of Type 2 DM (NIDDM)

A. Insulin Resistance: Male SD rats were intraperitoneally injected with insulin (Monotard®HM; Novo Nordisk, Bagsvaerd, Denmark, 0.5 IU/kg, tid) for 2 weeks. The development of insulin resistance is confirmed by a tolbutamide test (11).

B. NIDDM: Male SD rats were fasted for 48 hrs and anesthetized by intraperitoneal injection of pentobarbital at 30 mg/kg body weight. Animals were then injected with nicotinamide (100 mg/kg, ip) and streptozotocin (65 mg/kg, iv). Four weeks later, plasma glucose concentration was determined by the glucose oxidase method (Chemistry Analyzer; Autoanalyzer Quik-Lab., Ames, Spain). Animals with fasting blood sugar levels around 200 mg/dl and the development of an obese phenotype are classified as being induced to NIDDM.

Measurement of Blood Sugar

Normal, IDDM, and NIDDM SD rats were fasted for 8 hrs and anesthetized by pentobarbital (30 mg/kg, ip). Animals were fed with different dosages of resveratrol (0.05 mg, 0.1 mg, or 0.5 mg per kg body weight), and blood samples were then collected from femoral vein at the time points 0, 60, 90, and 120 min. Ten μl plasma was mixed with 1 ml glucose kit reagent and incubated at 37° C. for 10 min. The blood sugar level was determined as described. The blood sugar level was determined as described.

Statistical Analysis

Data were expressed as mean±standard error (S.E.). Statistical analysis was performed using ANOVA (analysis of variance) followed by Dunnett test, and the significant difference was set at $P<0.05$.

Results

Hypoglycemic Effect of Resveratrol in Normal SD Rats

Male SD rats were fed with resveratrol at 0.05 mg, 0.1 mg, or 0.5 mg per kg body weight and plasma glucose level was measured at 90 min after drug feeding. As shown in FIG. 1, resveratrol reduced blood sugar levels with a dose-dependent manner. Resveratrol reduced blood sugar by 25.72±4.03% and 35.53±2.0% at 0.1 mg/kg and 0.5 mg/kg, respectively.

Antihyperglycemic Effect of Resveratrol in IDDM SD Rats

Figure 2:
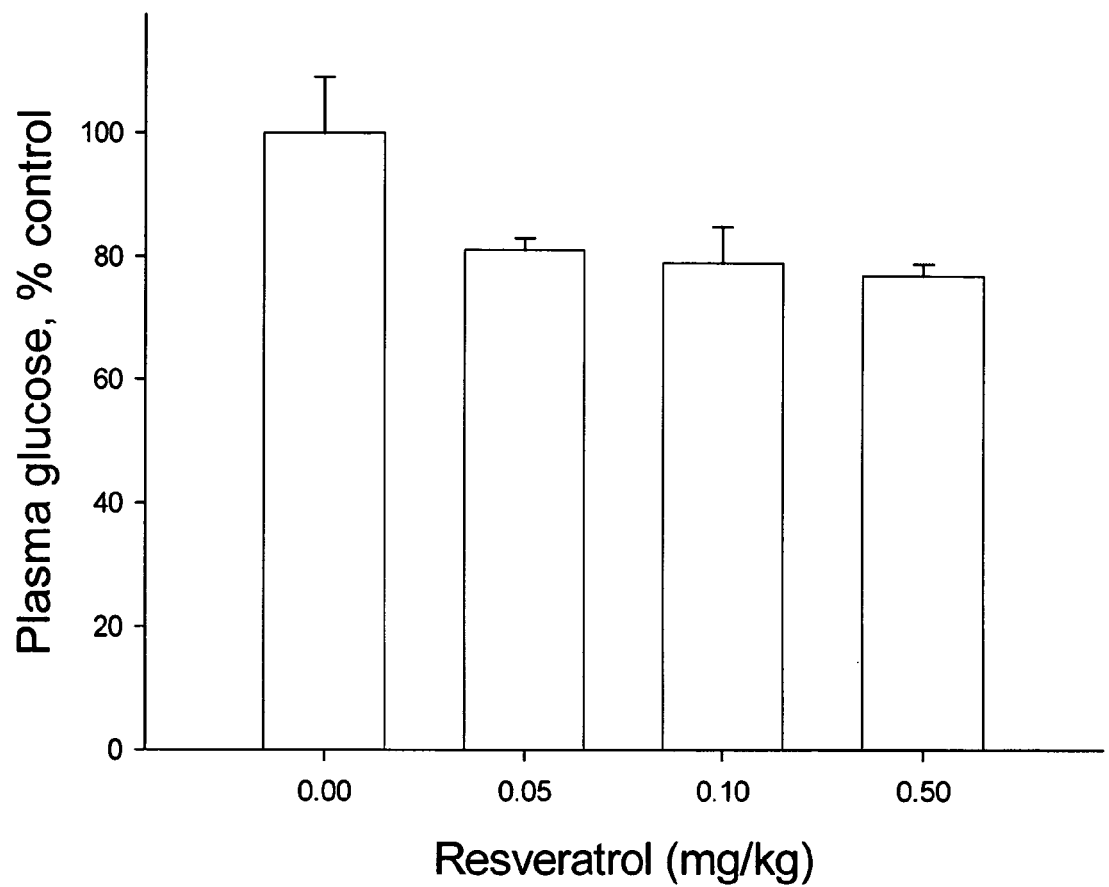
FIG. 2 is a bar graph of antihyperglycemic effect of resveratrol in IDDM SD rats.

IDDM SD rats were fed with resveratrol at 0.05 mg, 0.1 mg, or 0.5 mg per kg body weight and the blood sugar was measured at 90 min after drug feeding. Resveratrol at 0.1 mg and 0.5 mg per kg body weight, reduced blood sugar levels by 21.00±5.84% and 23.00±1.89%, respectively (FIG. 2).

Antihyperglycemic Effect of Resveratrol in NIDDM SD Rats

Figure 3:
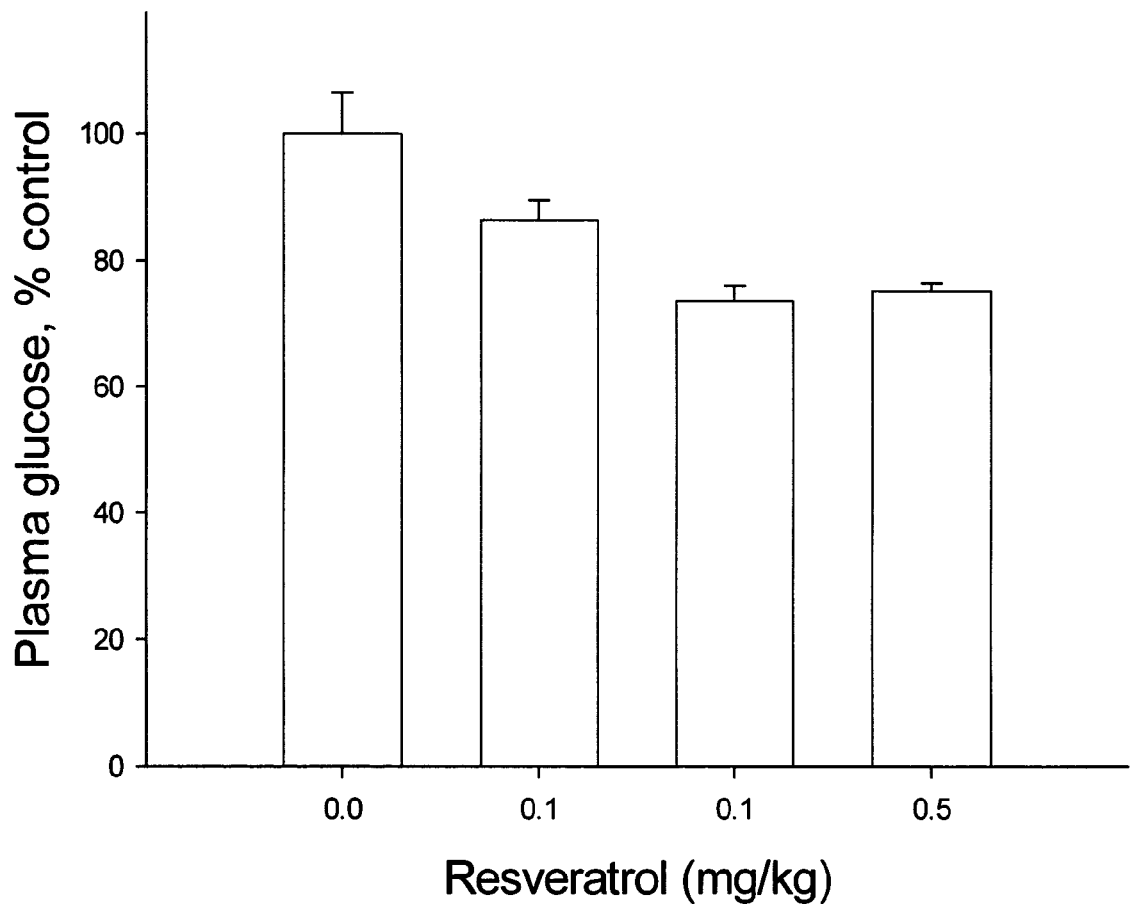
FIG. 3 is a bar graph of antihyperglycemic effect of resveratrol in NIDDM SD rats.
Figure 4:
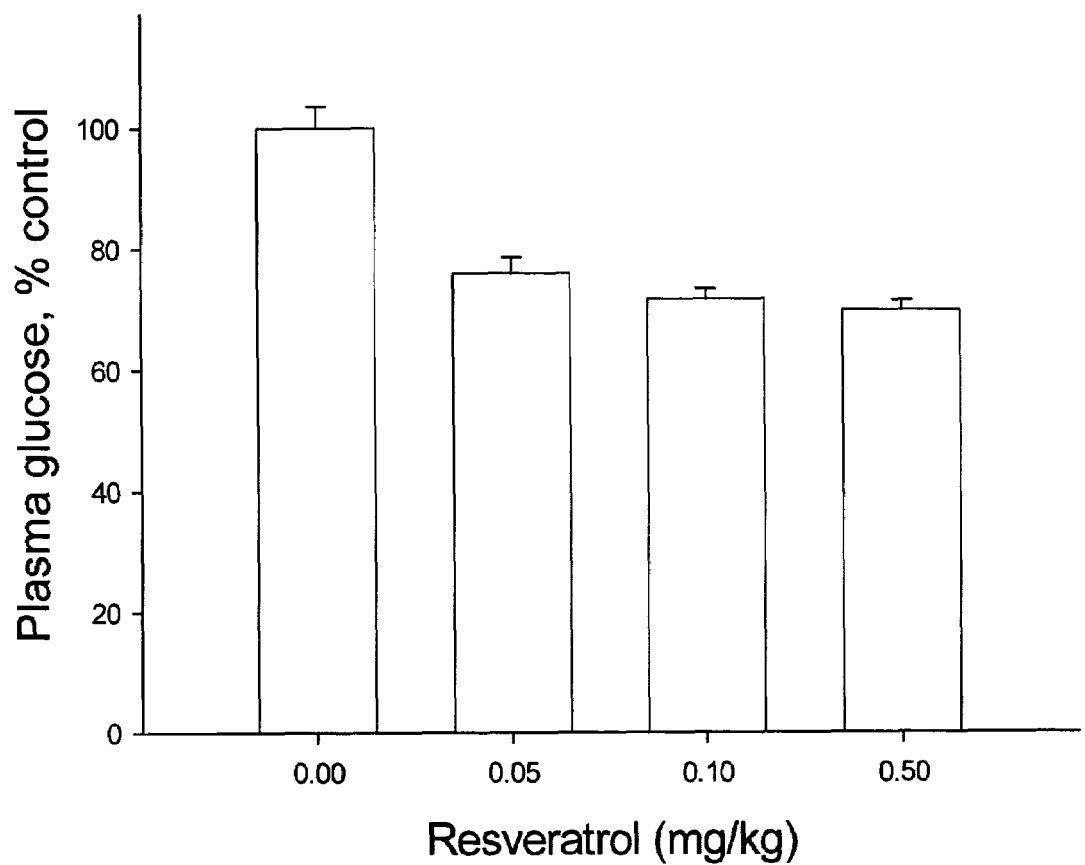
FIG. 4 is a bar graph of antihyperglycemic effect of resveratrol in insulin resistance SD rats.

NIDDM rats were fed with resveratrol and blood sugar was then measured as described. Resveratrol at 0.1 mg and 0.5 mg per kg body weight reduced blood sugar levels by 28.3±1.67% and 32.1±1.62%, respectively (FIG. 3). Moreover, in NIDDM insulin-resistant rats, administration of resveratrol also exhibited a dose-dependent hypoglycemic effect as that observed in NIDDM rats (FIG. 4)

Figure 5:
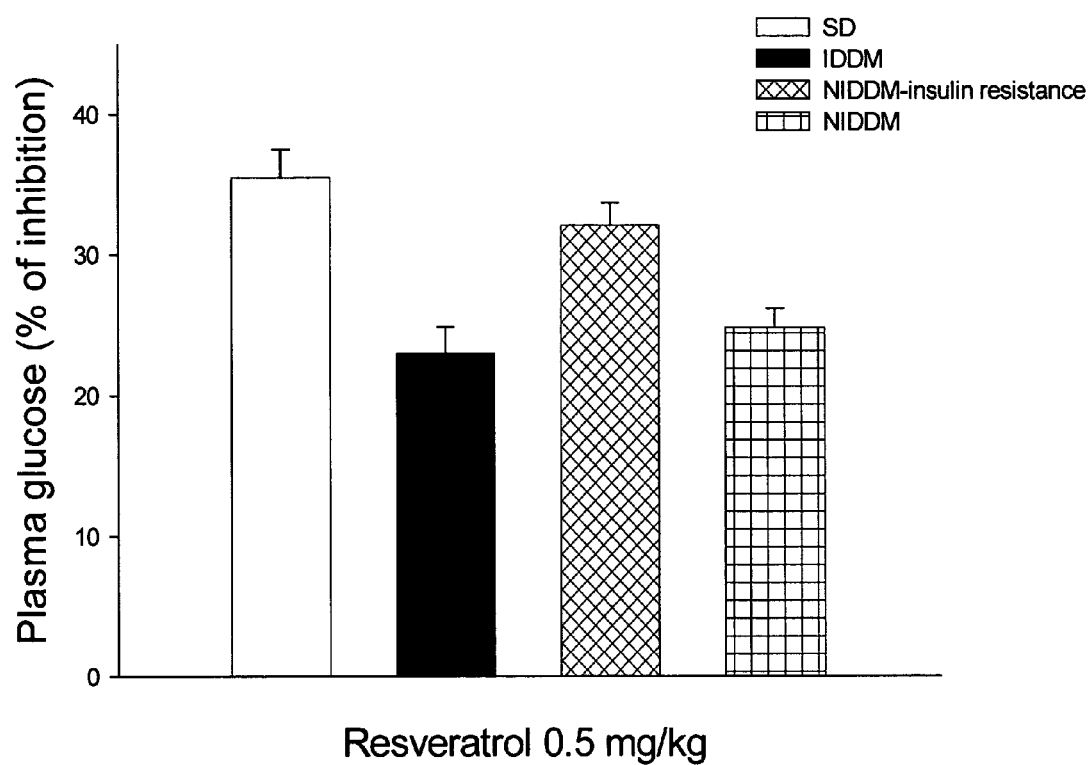
FIG. 5 is a bar graph of the comparison of the antihyperglycemic effect of resveratrol in normal, IDDM, insulin resistance and NIDDM SD rats.

Comparison of the Antihyperglycemic Efficacy of Resveratrol in Normal, IDDM, and NIDDM SD Rats Normal, IDDM, NIDDM, and NIDDM insulin-resistant SD rats (8 animals in each group) were all treated with resveratrol at 0.5 mg/kg. Ninety minutes after drug feeding, blood sugar was reduced by 35.53±2.0%, 23.00±1.89%, 24.86±1.32%, and 32.1±1.62%, in normal, IDDM, NIDDM, and NIDDM insulin-resistant rats, respectively compared to that of the untreated (no resvertrol) counterparts (FIG. 5).

Resveratrol Prolonged the Development of Insulin-Resistance in SD Rats

Figure 6:
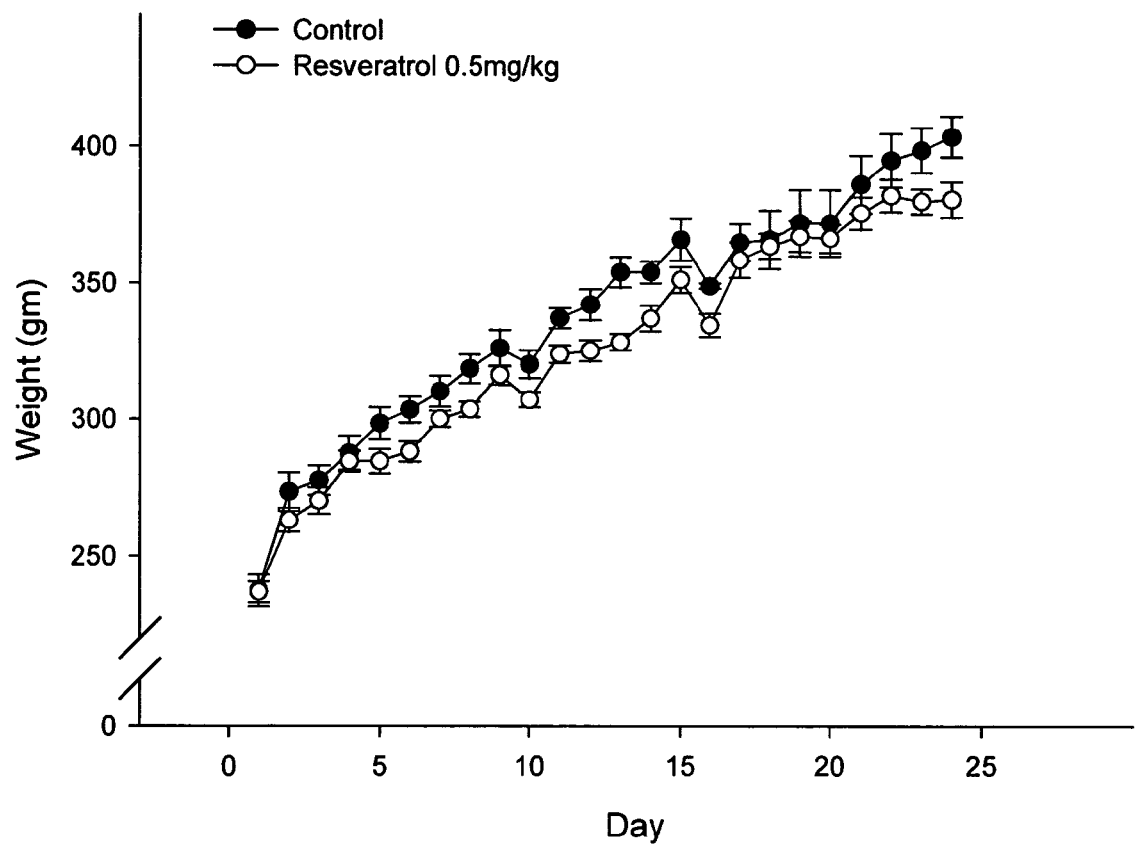
FIG. 6 shows that resveratrol slows down the body weight increment in insulin-resistant rats compared to untreated rats.

Male SD rats were intraperitoneally injected with insulin at 0.5 IU/kg, tid with or without resveratrol feeding (0.5 mg/kg BW, bid) Animals without resveratrol feeding started to develop insulin resistance on day 16.5±1.5. In contrast, development of insulin resistance in the resveratrol-fed animals was delayed till 23.5±1.5 days. In addition, resveratrol reduced the body weight increase by 6% compared with the untreated insulin-resistant animals (FIG. 6)

CONCLUSION

Resveratrol possessed antihyperglycemic efficacy in both IDDM and NIDDM animals. Moreover, resveratrol also delayed the development of insulin-resistance of the experimental animals and effectively slowed down the body weight increase of the insulin-resistant animals.

Although the invention has been explained in relation to its preferred embodiment, it is to be understood that many other possible modifications and variations can be made without departing from the spirit and scope of the invention as hereinafter claimed.

What is claimed is:

1. A method for measuring antihyperglycemic efficacy of resveratrol comprising:
   a: dividing rats into groups including a first, normal (untreated) Sprague-Dawley (SD) group, and second and third groups;
   b: pre-treating the second group with insulin-dependent diabetes mellitus (IDDM);
   c: pre-treating the third group with insulin-independent diabetes mellitus (NIDDM);
   d: feeding the rats of each of the second and third groups pre-treated with IDDM and NIDDM with a dosage of resveratrol;
   e: observing antihyperglycemic efficacy in the rats of each of the second and third groups pre-treated with IDDM and NIDDM after being fed resveratrol for a period of time; and
   f: injecting the rats of the first group of normal SD with insulin every day for a period of time and, in addition, feeding some of the rats of the first group of normal SD with resveratrol, and comparing antihyperglycemic efficacy of the rats of the first group of normal SD fed with resveratrol with the rats of the first group of normal SD given only insulin;
   wherein the resveratrol is dissolved in homemade saline solution and is irrigated into the stomach of the rats, and wherein feeding the rats of each of the second and third groups pre-treated with IDDM and NIDDM comprises dividing the rats of each of the second and third groups into three subgroups and feeding dosages of 0.05, 0.1 and 0.5 mg per kg body weight to the rats of the three subgroups respectively of each of the second and third groups of rats pretreated with IDDM and NIDDM.

2. The method as claimed in claim 1, wherein the rats of the first group of normal SD are eight weeks old, maintained under an ambient temperature of 25±1° C. and a light-dark period of 12 hrs, and fed with normal chow and water.

3. The method as claimed in claim 1, wherein observing and comparing antihyperglycemic efficacy comprises collecting blood samples from a femoral vein of the rats of the first, second, and third groups of rats at time points of 0, 60, 90 and 120 minutes after feeding the rats with the dosage of resveratrol.

4. A method for measuring antihyperglycemic efficacy of resveratrol comprising:
   a: dividing rats into groups including a first, normal (untreated) Sprague-Dawley (SD) group, and second and third groups;
   b: pre-treating the second group with insulin-dependent diabetes mellitus (IDDM);
   C: pre-treating the third group with insulin-independent diabetes mellitus (NIDDM);
   d: feeding the rats of each of the second and third groups pre-treated with IDDM and NIDDM with a dosage of resveratrol;
   e: observing antihyperglycemic efficacy in the rats of each of the second and third groups pre-treated with IDDM and NIDDM after being fed resveratrol for a period of time; and
   f: injecting the rats of the first group of normal SD with insulin every day for a period of time and, in addition, feeding some of the rats of the first group of normal SD with resveratrol, and comparing antihyperglycemic efficacy of the rats of the first group of normal SD fed with resveratrol with the rats of the first group of normal SD given only insulin;
   wherein pre-treating the second group of rats comprises fasting the second group of rats for 72 hrs, anesthetizing the fasted rats by intraperitoneal injection of pentobarbital at 30 mg/kg body weight, injecting the anesthetized rats with freshly prepared streptozotocin (STZ) solution at 65 mg/kg body weight intravenously, and three days later, measuring blood sugar, with the rats with blood sugar levels above 400 mg/dl and symptoms of polyphagia, polyuria and polydipsia being classified as being induced to the second group pre-treated with IDDM.

5. A method for measuring antihyperglycemic efficacy of resveratrol comprising:
- a: dividing rats into groups including a first, normal (untreated) Sprague-Dawley (SD) group, and second and third groups;
- b: pre-treating the second group with insulin-dependent diabetes mellitus (IDDM);
- c: pre-treating the third group with insulin-independent diabetes mellitus (NIDDM);
- d: feeding the rats of each of the second and third groups pre-treated with IDDM and NIDDM with a dosage of resveratrol;
- e: observing antihyperglycemic efficacy in the rats of each of the second and third groups pre-treated with IDDM and NIDDM after being fed resveratrol for a period of time; and
- f: injecting the rats of the first group of normal SD with insulin every day for a period of time and, in addition, feeding some of the rats of the first group of normal SD with resveratrol, and comparing antihyperglycemic efficacy of the rats of the first group of normal SD fed with resveratrol with the rats of the first group of normal SD given only insulin;

wherein pre-treating the third group of rats comprises fasting the third group of rats for 48 hrs, anesthetizing the fasted rats by intraperitoneal injection of pentobarbital at 30 mg/kg body weight and injected with nicotinamide (100 mg/kg, ip) and streptozotocin (65 mg/kg, iv), and four weeks later, determining plasma glucose concentration by a glucose oxidase method, with fasting blood sugar levels around 200 mg/dl and development of an obese phenotype being classified as being induced to the third group pre-treated with NIDDM.

* * * * *